United States Patent [19]
Shelton et al.

[11] Patent Number: 5,606,746
[45] Date of Patent: Mar. 4, 1997

[54] COOL-LIFE VEST WITH DETACHABLE HOOD

[76] Inventors: Terri Shelton; Steven Barger, both of 2521 W. Augusta Ave., Phoenix, Ariz. 85051

[21] Appl. No.: 360,566

[22] Filed: Dec. 21, 1994

[51] Int. Cl.⁶ ............................. A41D 1/04; A41D 13/00
[52] U.S. Cl. .................... 2/102; 2/7; 2/84; 2/94
[58] Field of Search ................... 2/102, 84, 94, 2/7, 8, 81, 171.2, 411, 2; 607/108, 109, 110; 62/259.3

[56] References Cited

U.S. PATENT DOCUMENTS

| | | | |
|---|---|---|---|
| 1,485,392 | 3/1924 | Halek | 2/84 |
| 2,049,723 | 8/1936 | Pomeranz | 2/7 |
| 3,134,891 | 5/1964 | Hyer | 607/109 |
| 3,839,621 | 10/1974 | Hariu | 607/109 |
| 4,204,543 | 5/1980 | Henderson | 2/7 |
| 4,601,067 | 7/1986 | Buonassissi | 2/2.5 |
| 4,908,248 | 3/1990 | Nakashima et al. | 428/355 |
| 5,005,374 | 4/1991 | Spitler | 2/7 |
| 5,072,455 | 12/1991 | St. Ours | 2/102 |
| 5,146,625 | 9/1992 | Steele et al. | 2/102 |
| 5,206,957 | 5/1993 | Gulick | 2/102 |
| 5,274,850 | 1/1994 | Aldridge | 2/81 |

*Primary Examiner*—Amy B. Vanatta

[57] ABSTRACT

An article of clothing including a vest portion and a detachable hood having a polyacrylamide copolymer filler that cools the body by activating the cooling stage, which is done by placing the vest and hood in water for the required time or placing the vest and hood in ice water for required time. Top and bottom pieces of material (10), (12) will dry and the filler (14) will remain cool and moist. They are worn by placing on the body and attaching fasteners and will keep the individual cool for hours. They are made of materials that can be washed by the individual. They can be stored for days in plastic bags in the refrigerator. If long-term storage is needed, it can be accomplished by line-drying and then put away until ready for use again.

5 Claims, 6 Drawing Sheets

COOL-LIFE VEST WITH DETACHABLE HOOD

BACKGROUND—FIELD OF INVENTION

This invention relates to an article of clothing, specifically to such clothing which, when worn, is used to cool the body.

BACKGROUND—DESCRIPTION OF PRIOR ART

Originally, the way people try to cool down when they become hot does not always work well or last for any length of time.

a) Sometimes, people remove some of their clothing when they are too hot. This is at times impossible for some of us to do, especially if wearing a uniform that represents the organization that you are working for;

b) At times people that work outdoors remove their shirts and wet them with water before putting them on again. This is a short-term way of cooling down because after the shirt dries you become hot again;

c) Other times people, when possible, retreat to air cooled rooms to cool down, but there are many people in this world that do not have access to that comfort when they need it;

d) Fire fighters use a wet towel over their heads to cool down after putting out a fire. They also use ice in bags. The problem with this is that a wet cool towel soon becomes a hot towel and ice soon melts;

e) We could also use a spray-type bottle to mist ourselves or sit under a misting system. This tends to be a short-term relief from the heat, because once we stop spraying mist from the bottle or move from the spray of a misting system, we, in a very short time, become hot again.

Objects and Advantages of the proposed Cool-Life Vest

Accordingly, several objects and advantages of the Cool-Life Vest with Detachable Hood are:

a) The wearer of the Cool-Life Vest with Detachable Hood will not have to remove any clothing to cool down. It can be worn directly over any clothing or uniform;

b) After the initial chilling procedure of the Cool-Life Vest with Detachable Hood, it will remain cool for several hours while worn;

c) All that is needed to re-chill the Cool-Life Vest with Detachable Hood is a refrigerator or an ice chest with either ice water or plastic freezer packs;

d) Fire fighters, or anyone that works or plays in the heat can benefit from wearing it because, they can cool down fast and safe as well, and stay that way for a long time while wearing the Cool-Life Vest with Detachable Hood;

e) The Cool-Life Vest with Detachable Hood can be worn with comfort. It can be worn while you are on the go, or being stationary. It can be worn with casual wear or any uniform and it has a good appearance;

f) The cost is very reasonable compared to the time of cooling that is received from it.

Further objects and advantages of the Cool-Life Vest with Detachable Hood will become apparent from a consideration of the drawings and ensuing description.

DRAWING FIGURES

In the drawings, closely related figures have the same number but different alphabetic suffixes.

REFERENCE NUMERALS IN DRAWINGS

| | | | |
|---|---|---|---|
| 10 | Top piece of material | 12 | Underneath piece of material |
| 14 | Filler (a non-toxic synthetic polyacrylamide co-polymer) | 16 | Trim material or edging |
| | | 20 | Fasteners or closures for vest |
| 18 | Detachable Hood | | |
| 22 | Fasteners on hood for vest | | |

DESCRIPTION—FIGS. 1 TO 5

Figure 1:
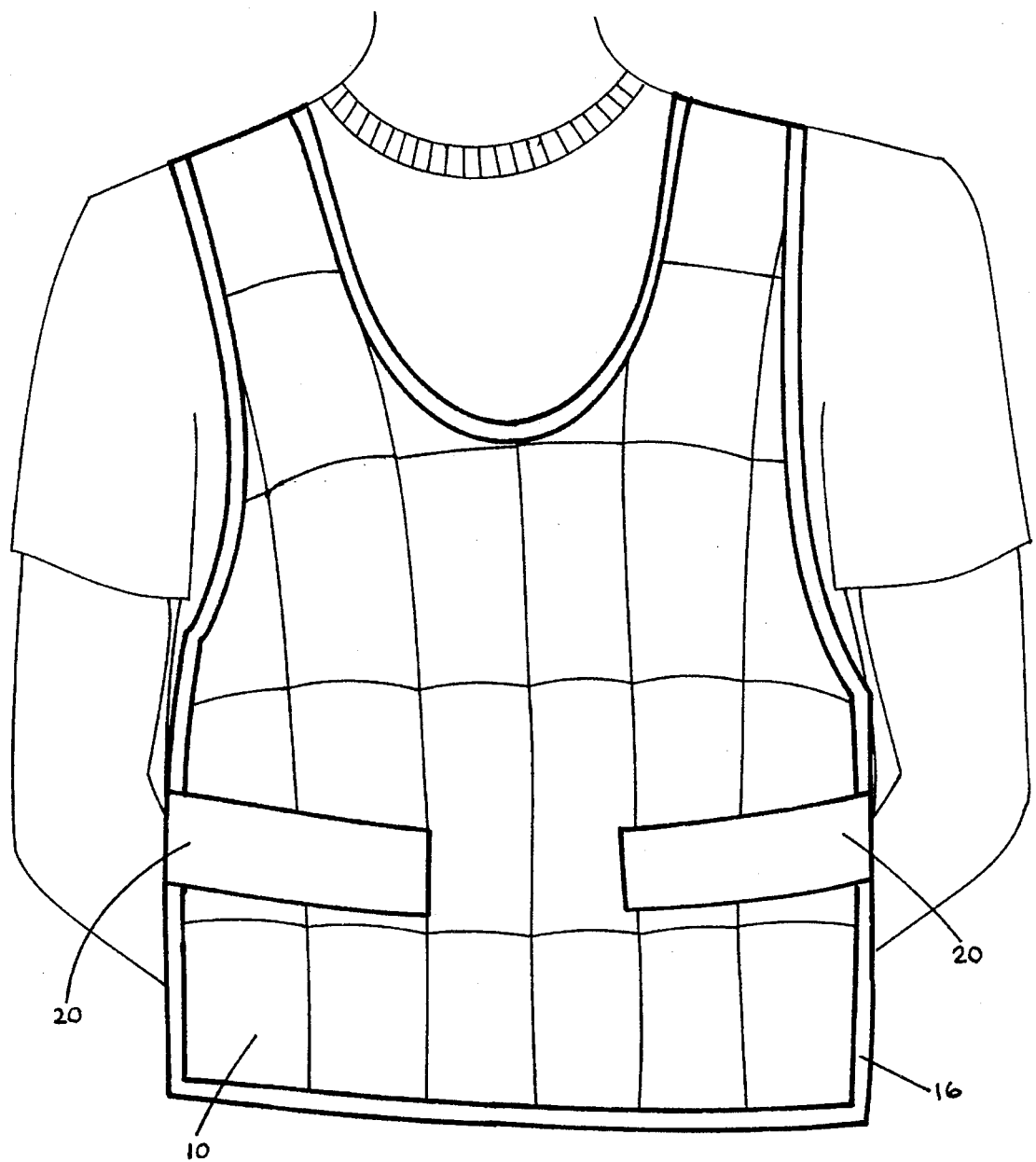
FIG. 1 is front view showing the Cool-Life Vest.
Figure 1A:
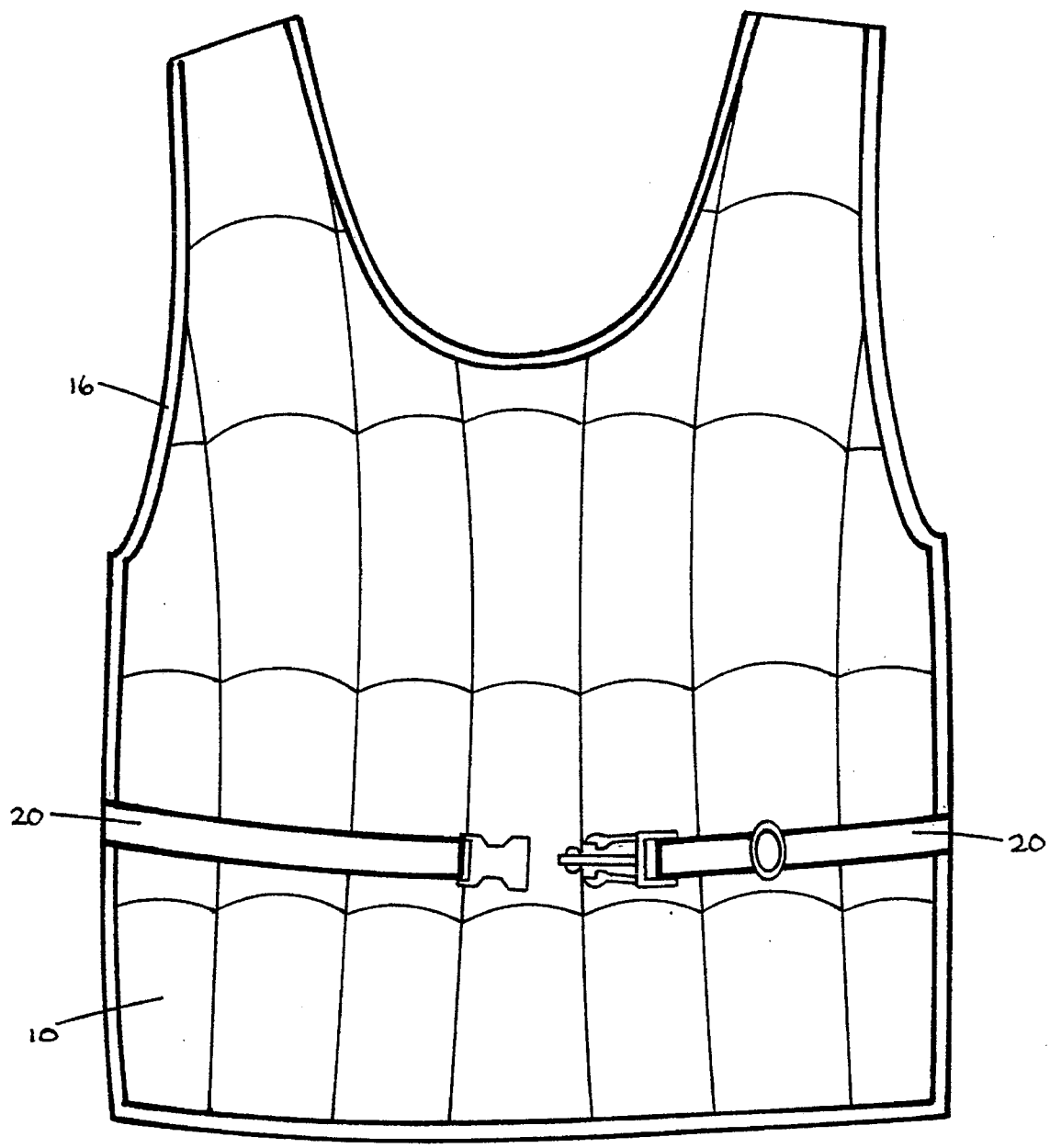
FIG. 1A is front view with a different type of fastener used.
Figure 2:
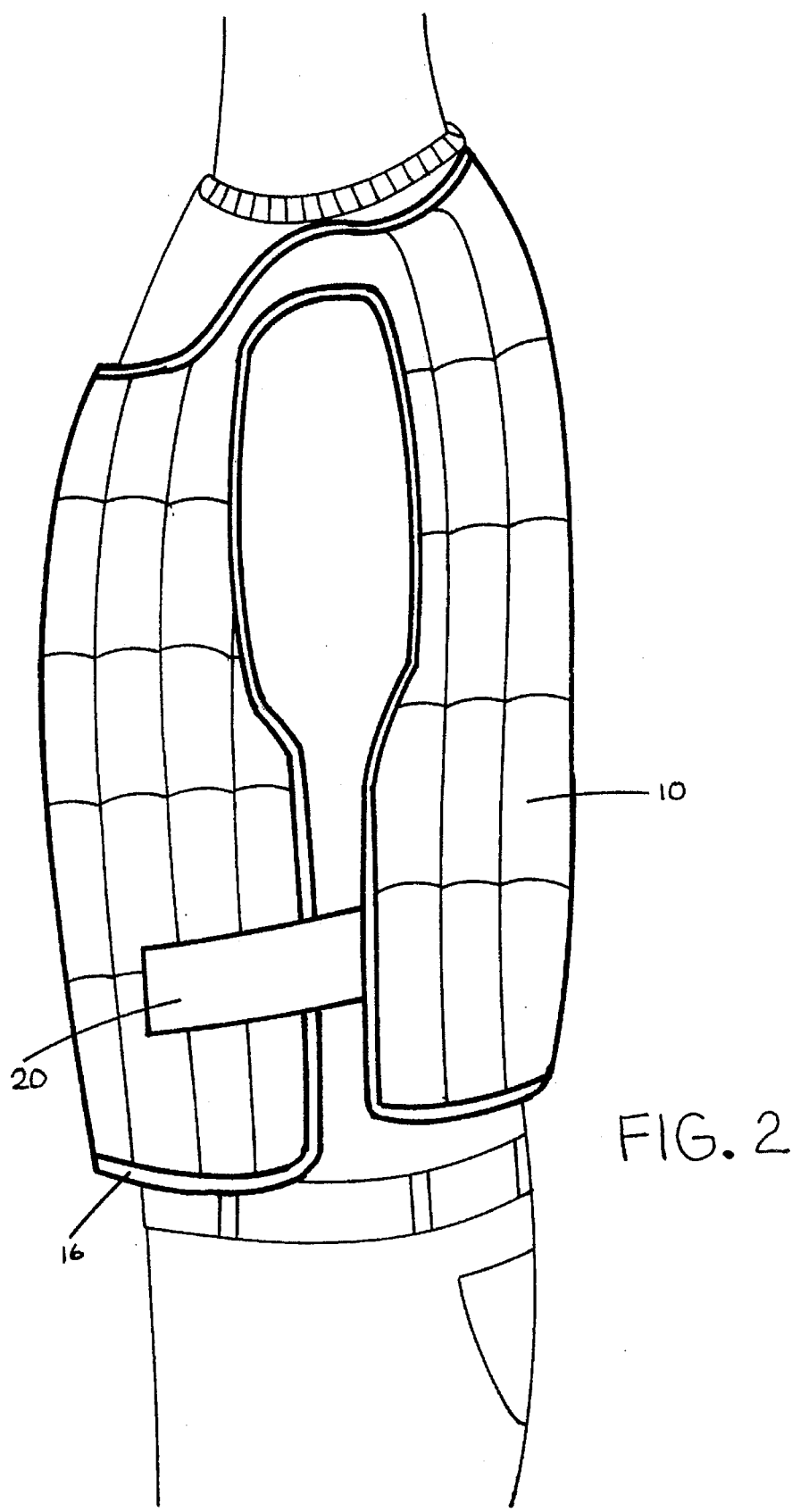
FIG. 2 is a side view showing the Cool-Life Vest.
Figure 3:
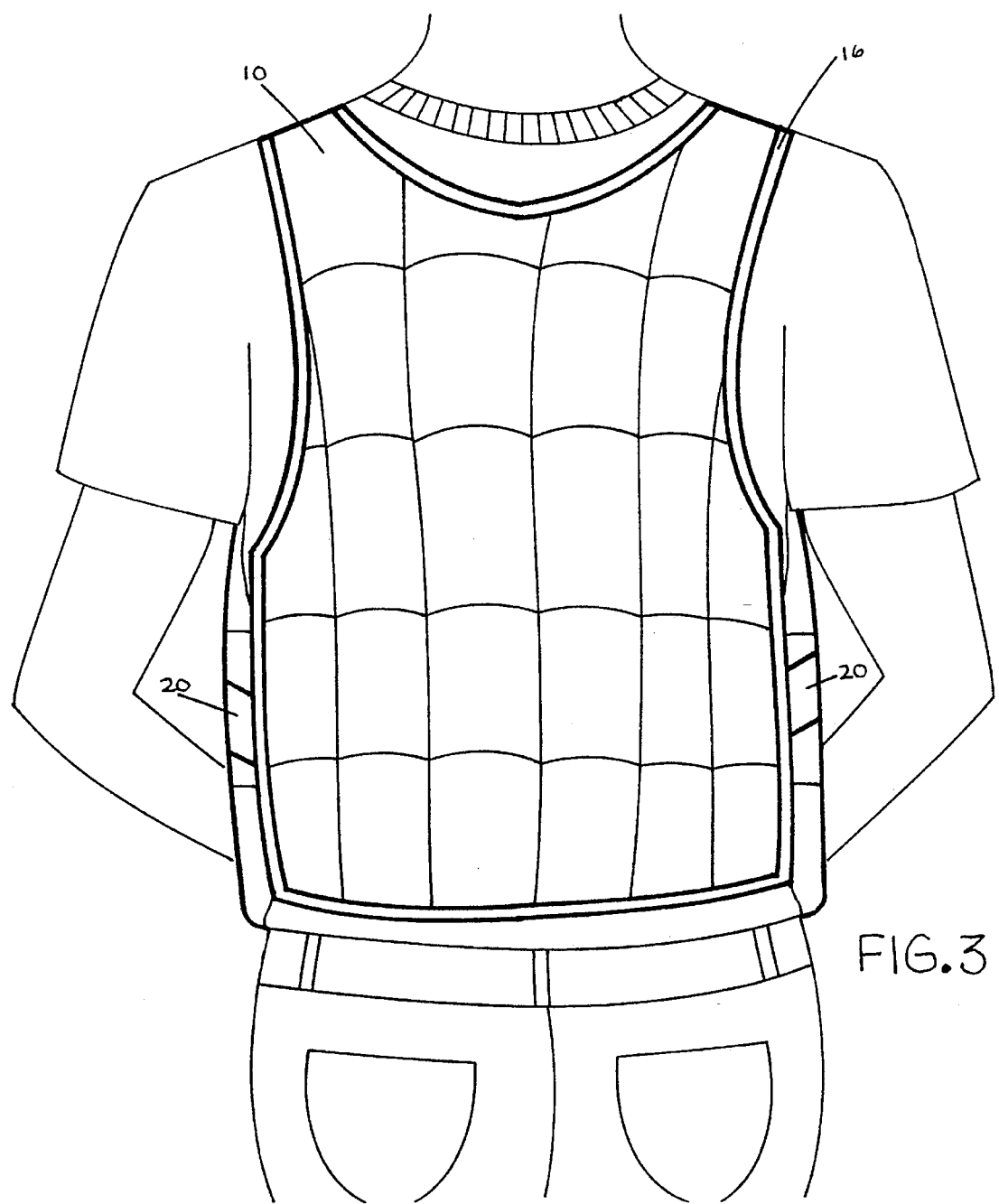
FIG. 3 is a rear view showing the Cool-Life Vest.
Figure 4:
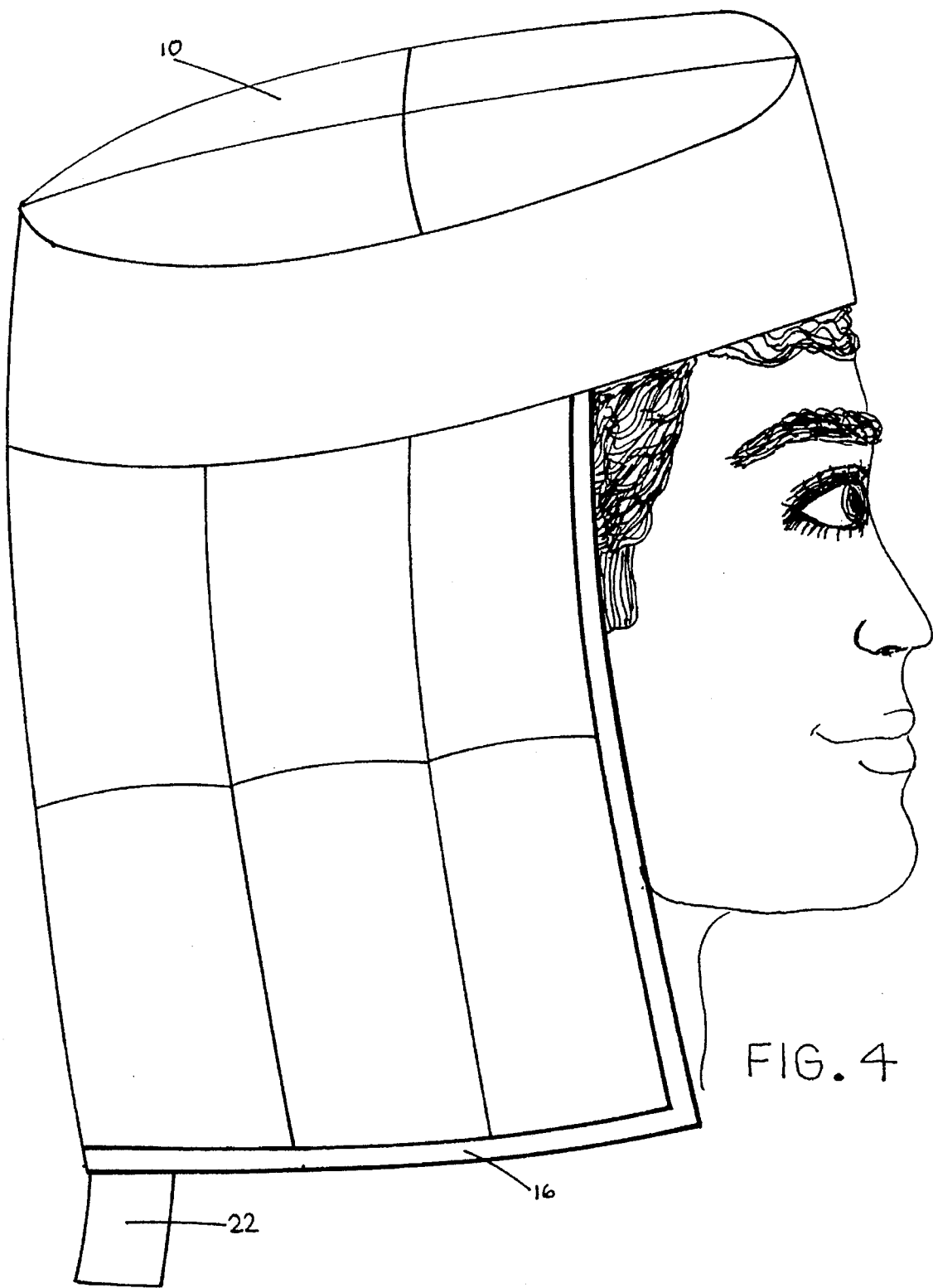
FIG. 4 is the Detachable Hood that attaches to the Cool-Life Vest with fasteners.
Figure 5:
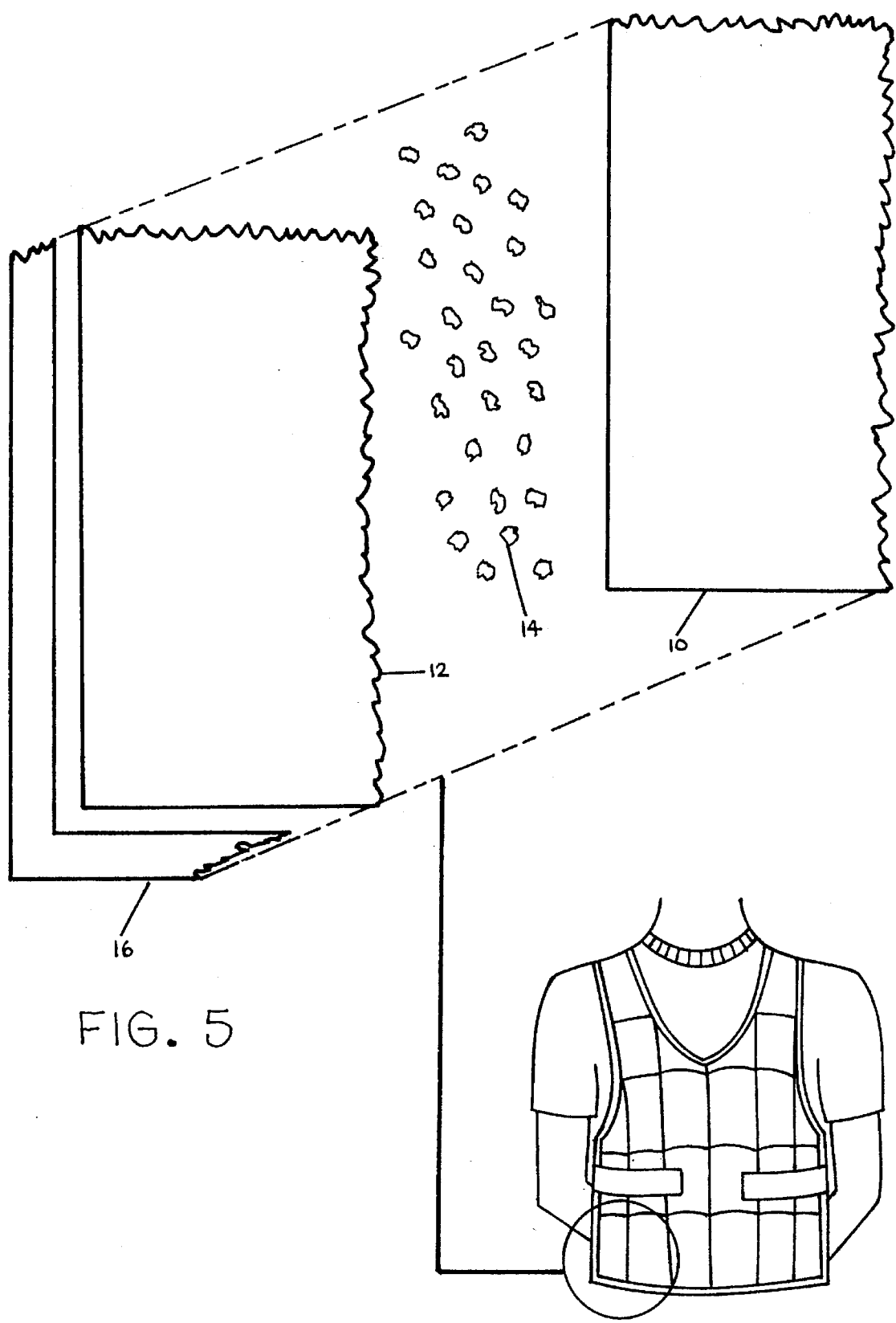
FIG. 5 is an exploded view of the layers used to make the Cool-Life Vest with Detachable Hood.

FIG. 1, 1A, and 3 show the front view and the back view of the Cool-Life Vest. The vest comprises of a top piece of material 10, and a underneath piece of material 12, sewn together from the inside of both. A fastener or closure 20 is sewn on each side of vest in between top piece of material 10, and underneath piece of material 12. Bottom of vest is left open to make room for the adding of a filler 14. The neck of the vest is also left open to allow for seamstress to turn right side out. After vest is turned right side out, neck is sewn shut. The bottom is still left open. Sections are then sewn with equal spacing vertically through top piece of material 10, and underneath piece of material 12 of the front FIG. 1 and the back FIG. 3. These sections are where the filler 14 will be added. Insert filler 14 in small amounts and sew horizontally to make sections. Add more filler 14, then sew horizontally. Keep doing this until the bottom of vest has been reached on both sides of vest. At this point, sew bottom of vest shut and add trim or edging material 16 to neck, sides of vest, and bottom of vest.

The Detachable Hood 18 is made in a similar way. Take a top piece of material 10, and a underneath piece of material 12, sew together from the inside of both. Leave an opening to turn right side out. It will also to be used to add filler 14. Turn right side out and sew sections of equal spacing in Detachable Hood 18. Start adding small amounts of filler 14. Sew sections shut. Add more filler 14 and sew those sections shut. This is to be done until the bottom of Detachable Hood 18 has been reached. Add the trim material or edging 16 to bottom of Detachable Hood 18. Add fasteners 22 to bottom back of Detachable Hood 18. They will be attached to back neck area of vest.

From the description above, a number of advantages of our Cool-Life Vest with Detachable Hood become evident.

a) It can be made in any color to go with any uniform or in a print material for a more casual look.

b) It can be made in all sizes to fit small or large.

c) It can very easily be in different cuts, such as with an opening in the front and sides, or an opening in the front only, or an opening in the sides only.

d) It can be put on easily and quickly and worn with comfort.

OPERATION—FIGS. 1, 1A, 2, 3, 4, 5

The manner of using the Cool-Life Vest with Detachable Hood is simple. Namely, one first places it in a sink of cold water for one and one half (1½) hours. This will cause the filler 14 to absorb water, thus expanding the sections that were sewn in the vest.

After the required time in water, remove the Cool-Life Vest with Detachable Hood and allow some of the excess water to drip from it.

At this time it is ready to be chilled. Place it inside the refrigerator for 2 hours or, if not needed for use at that time, it may stay in refrigerator longer.

When the Cool-Life Vest with Detachable Hood has chilled remove it from the refrigerator. Put it on and attach fasteners or closures to hold it close to the body. The top piece of material 10 and the underneath piece of material 12 will dry, and the filler 14 will remain cool and moist.

Another way of using The Cool-Life Vest with Detachable Hood is by placing it in an ice chest with ice water for one and one half (1½) hours for the initial chilling.

After the chilling, remove it and allow some of the excess water to drip off. Then it may be put on.

After the initial wetting, it may be cooled by refrigerating or by ice chest with ice water or plastic ice packs. It can also be stored in a plastic bag in the refrigerator for days without wetting it again.

If the Cool-Life Vest with Detachable Hood is not to be worn for months at a time, it will need to go through a drying stage. This can be accomplished by line-drying it until the filler 14 is dry and reduced back to its crystal stage. This takes anywhere from three to four days depending on the temperature outdoors. It can also be line-dried indoors. It will then be ready for storage for the next time it is needed.

It may be washed after the drying stage. Quickly wash it by hand in a mild liquid detergent. Rinse it well and either line-dry it or put it in cold water to activate the chilling stage again.

SUMMARY, RAMIFICATIONS, AND SCOPE

Accordingly, the reader will see that the Cool-Life Vest with Detachable Hood is a highly reliable, economical way to cool down that anyone young or old can use in work or play.

it permits fire fighters to have a long-lasting coolness during or after working in a fire;

it permits the wearer to remain totally clothed while cooling down;

it provides several hours of cooling;

it provides anyone that works or plays outdoors in the heat to be cool while active or stationary.

While our description contains many specificities, these should not be construed as limitations on the scope of the invention, but rather as an exemplification of some preferred embodiments thereof. Many other variations are possible. For example, it can be in any color; such as a solid or print; sizes can range to fit anyone; the cut can easily be changed; an opening in the front or opening on the sides or both; fasteners or closures could be Velcro-like; rings and material; parachute hooks; elastic could be added to any of these; it can be worn with or without the hood; the sewing of the sections could be added in any design pattern.

Thus the scope of the invention should be determined by the appended claims and their legal equivalents, rather than by the examples given.

We claim:

1. A one-piece, cooling vest for wearing over any casual clothing or work uniform, comprising:

a vest portion comprising a double-layer of material said material being a cotton-polyester mix sized and configured to be worn around a wearer's upper body from waist to shoulder, said double-layer of material comprising one layer of light-weight fabric material secured by sewing to another layer of light-weight fabric material, and a filler permanently disposed between the sewn layers of material throughout the entire cooling vest, said filler comprising a water permeable non-toxic, synthetic, polyacrylamide co-polymer in crystal form;

a detachable cooling hood connected to an upper back region of said vest portion by hook and loop fasteners, said detachable cooling hood comprising a double-layer of material, said double-layer of material comprising one layer of light-weight fabric material secured by sewing to another layer of light-weight fabric material, and a filler permanently disposed between the sewn layers of material throughout the entire cooling hood, said filler comprising a water permeable non-toxic, synthetic, polyacrylamide co-polymer in crystal form.

2. A cooling vest according to claim 1, wherein said vest portion has a side opening on each side of the vest, said side opening including hook and loop fastening means for adjustably tightening the side openings to hold the cooling vest snugly to the body.

3. A cooling vest according to claim 1, wherein said vest portion has a side opening on each side of the vest, said side opening including woven strap and parachute hook fastening means for adjustably tightening the side openings to hold the cooling vest snugly to the body.

4. A cooling vest according to claim 1, wherein said filler expands when said vest portion and said hood are submerged in water, and when said vest portion and said hood are removed to allow excess water to drip and are then placed in a refrigerated area for three hours to chill, said filler provides hours of long-lasting cooling.

5. A cooling vest according to claim 1, wherein said vest portion and said hood are machine washable whenever said vest portion and said hood become soiled.

\* \* \* \* \*